(12) United States Patent
Shimazaki et al.

(10) Patent No.: US 7,332,809 B2
(45) Date of Patent: Feb. 19, 2008

(54) GLASS SUBSTRATE HAVING A GROOVED PORTION, METHOD FOR FABRICATING THE SAME, AND PRESS MOLD FOR FABRICATING THE GLASS SUBSTRATE

(75) Inventors: Takeshi Shimazaki, Yokohama (JP); Masatoshi Ohyama, Yokohama (JP); Hiroshi Wakatsuki, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 109 days.

(21) Appl. No.: 11/234,340

(22) Filed: Sep. 26, 2005

(65) Prior Publication Data

US 2006/0022349 A1    Feb. 2, 2006

Related U.S. Application Data

(63) Continuation of application No. PCT/JP2004/004200, filed on Mar. 25, 2004.

(30) Foreign Application Priority Data

Mar. 25, 2003    (JP)    ............................. 2003-082634

(51) Int. Cl.
*H01L 23/06*    (2006.01)
(52) U.S. Cl. ............................. 257/729; 257/E23.009; 385/137

(58) Field of Classification Search .................. 257/729
See application file for complete search history.

(56) References Cited

U.S. PATENT DOCUMENTS 6,240,235 B1 * 5/2001 Uno et al. .................. 385/137
6,324,332 B1 * 11/2001 Yamashita et al. .......... 385/137

FOREIGN PATENT DOCUMENTS

| JP | 9-120014 | 5/1997 |
| JP | 11-160562 | 6/1999 |
| JP | 11-194226 | 7/1999 |
| JP | 2000-347060 | 12/2000 |
| JP | 2002-72016 | 3/2002 |
| WO | WO 97/15850 | 5/1997 |
| WO | WO 02/065138 | 8/2002 |

* cited by examiner

*Primary Examiner*—Tu-Tu V. Ho
(74) *Attorney, Agent, or Firm*—Oblon, Spivak, McClelland, Maier & Neustadt, P.C.

(57) ABSTRACT

A press mold for fabricating a glass substrate, the glass substrate comprising a substrate; and a terrace-shaped flat portion formed on the substrate and having a grooved portion formed therein, is characterized in that the press mold comprises a top mold and a bottom mold; at least one of the top mold and the bottom mold having an indented portion formed therein so as to correspond to the terrace-shaped flat portion, the indented portion having an entire periphery surrounded by a mold reference surface.

7 Claims, 6 Drawing Sheets

GLASS SUBSTRATE HAVING A GROOVED PORTION, METHOD FOR FABRICATING THE SAME, AND PRESS MOLD FOR FABRICATING THE GLASS SUBSTRATE

BACKGROUND OF THE INVENTION

1. Field of the Invention

The present invention relates to a glass substrate including a grooved portion formed in a micron structure in a terrace-shaped flat portion formed on a substrate, such as a micro-reactor chip, a substrate for microanalysis or an optical fiber fixing substrate, a method for fabricating the same, and a press mold for fabricating the glass substrate.

2. Discussion of Related Art

In the field of optical communication, there has been known an optical fiber fixing substrate, which brings opposed end portions of optical fibers into alignment with each other and fixes both opposed end portions for connection of plural optical fibers or plural optical fibers and other elements, such as light guides (for example, JP-A-11-194226, pages 5 and 6, FIG. 1 and FIG. 4).

This optical fiber fixing substrate includes an optical fiber engaging portion having V-shaped grooves formed therein to engage (put) opposed end portions of optical fibers therein, and stoppers for adhesive flow formed both sides of the optical fiber engaging portion, wherein the end portions of the optical fibers are engaged with the optical fiber engaging portion, and an adhesive is filled in the optical fiber engaging portion, and a pressing member is covered from above the optical fiber engaging portion to fix the end portions of the optical fibers between the optical fiber fixing substrate and the pressing member. In this case, the adhesive, which is filled in the optical fiber engaging portion, can be prevented from leaking out of the optical fiber engaging portion by the provision of the stoppers for adhesive flow.

This optical fiber fixing substrate is made of glass. The substrate is fabricated by being pressed by a forming mold, which is ground by a grinding wheel. Additionally, the tops of the V-shaped grooves are chamfered in an arcuate shape.

Although the optical fiber fixing substrate disclosed in JP-A-11-194226 has the tops of the V-shaped grooves chamfered in an arcuate shape, the other portions of the substrate are not chamfered. Since there is a possibility that any one of the other portions is inadvertently chipped to damage an optical fiber, there is a problem that handling is difficult. Since the optical fiber fixing substrate disclosed in JP-A-11-194226 has only the tops of the V-shaped grooves chamfered, there is another problem that any one of the tops is likely to be chipped when contacting another member.

By the way, a micro-reactor chip or a substrate for microanalysis has been known as a substrate comprising a glass substrate base material having grooves formed in a micron structure (in microns), such as an optical fiber fixing substrate. Such a micro-reactor chip or such a substrate for microanalysis has a flat portion formed with grooves in microns for flowing a solution and has a problem that trouble is caused in reaction or analysis when a groove is chipped. Additionally, it is necessary to strictly control a flow rate in these applications. Although a cover, such as a glass sheet in a flat shape, is put over the grooves for forming flow passages, there is a possibility that a flow rate fails to be sufficiently controlled unless the flat portion in addition to the shape of the grooves has necessary molding precision.

SUMMARY OF THE INVENTION

The present invention is proposed in consideration of such circumstances. It is an object to provide a substrate capable of suppressing the occurrence of a chip, a method for fabricating the substrate, and a press mold for fabricating the glass substrate, which is appropriate for the substrate and the method.

The present invention can attain the object and provide the following modes.

1) A press mold for fabricating a glass substrate, the glass substrate comprising a substrate; and a terrace-shaped flat portion formed on the substrate and having a grooved portion formed therein;

the press mold comprising:

a top mold and a bottom mold;

at least one of the top mold and the bottom mold having an indented portion formed therein so as to correspond to the terrace-shaped flat portion, the indented portion having an entire periphery surrounded by a mold reference surface; and a convex portion formed in the indented portion so as to correspond to the grooved portion.

2) The press mold according to item 1), wherein a boundary portion between the indented portion and the convex portion is arcuately chamfered.

3) The press mold according to item 1 or 2, wherein a depth of the indented portion is greater than a height of the convex portion.

4) The press mold according to item 1) or 2), wherein the convex portion corresponds to a V-shaped groove.

5) The press mold according to item 1) or 2), wherein the convex portion corresponds to a flow passage for a fluid.

6) A method for fabricating a glass substrate by using the press mold defined in any one of items 1) to 5) to heat-press glass.

7) A glass substrate comprising:

a substrate;

a terrace-shaped flat portion formed on the substrate and having a grooved portion formed in a micron structure therein; and a boundary portion between the terrace-shaped flat portion formed on the substrate and the grooved portion being arcuately chamfered.

8) The glass substrate according to item 7), wherein the grooved portion serves as a flow passage for a fluid.

9) The glass substrate according to Claim 8), which is directed to a micro-reactor chip or a substrate for microanalysis.

10) An optical fiber fixing substrate comprising:

a grooved portion formed thereon to fix an end portion of an optical fiber;

the substrate comprising a substrate body having a flat portion; and a terrace-shaped flat portion including the grooved portion formed on the substrate and having a groove formed in the grooved portion, and bonding projections formed on both sides of the grooved portion so as to sandwich the grooved portion therebetween and to be higher than the flat portion;

wherein a top of the groove, a boundary portion between the grooved portion and each of the bonding projections, and ridge portions of the bonding projections are arcuately chamfered.

11) The optical fiber fixing substrate according to item 10), wherein each of the bonding projections has a cut-out portion formed on an outer side thereof.

12) The optical fiber fixing substrate according to item 10 or 11, wherein a boundary portion between adjacent surfaces of the cut-out portion is arcuately chamfered.

13) A method for fabricating an optical fiber fixing substrate in a single pressing step, applying heat and pressures to the substrate by a mold member, the optical fiber fixing substrate defined in item 10), 11) or 12), and the mold member having a concave and convex portion for forming the grooved portion, concave portions for forming the bonding projections, and convex portions for forming the cut-out portions, wherein the concave and convex portion and the concave portions are formed in an indented portion surrounded by an entire periphery of a mold reference surface forming flat surfaces of the convex portions.

In accordance with the present invention, the press mold comprises the top mold and the bottom mold, at least one of the top mold and the bottom mold having the indented portion formed therein so as to correspond to the terrace-shaped flat portion to be formed in the substrate, the indented portion having the entire periphery surrounded by the mold reference surface, the convex portion formed in the indented portion so as to correspond to the grooved portion. Glass as an object to be pressed can have a mold surface of the press mold faithfully transferred thereonto since the object is pressed, being confined in the indented portion. Accordingly, it is possible to obtain a glass substrate with excellent molding precision.

According to the mode defined in item 2), the boundary portion between the indented portion and the convex portion is arcuately chamfered. A glass substrate obtained by pressing can suppress the grooved portion from being chipped since the boundary portion between the flat portion of the substrate and the grooved portion formed in a micro structure (in a micron order) is arcuately chamfered.

According to the mode defined in item 3), the depth of the indented portion is greater than the height of the convex portion. Accordingly, it is easy to handle the press mold since a leading edge of the convex portion is hardly susceptible to be damaged or deformed. Additionally, it is possible to prevent damage to a product, which is put in the grooved portion, when the press mold is used as a jig.

According to the mode defined in item 4), the mold surface of the press mold can be faithfully transferred since the convex portion corresponds to the V-shaped groove. Accordingly, it is possible to obtain an optical fiber fixing substrate with excellent molding precision.

According to the mode defined in item 5), the convex portion corresponds to the flow passage for a fluid. Accordingly, the glass substrate formed by the press mold can be used as a micro flow passage having excellent molding precision and prevent the occurrence of a chip in the grooved portion.

According to the mode defined in item 6), it is characterized in that glass is heat-pressed by the press mold defined in any one of items 1) to 5). Accordingly, it is possible to obtain a glass substrate with the grooved portion, which has excellent molding precision.

According to the mode defined in item 7), it is possible to restrain a grooved portion from being chipped since the boundary portion between the terrace-shaped flat portion formed on the substrate and the grooved portion formed in a micron structure (in microns) is arcuately chamfered. Examples of the substrate are a micro-reactor chip and a substrate for microanalysis as recited in Claim 9. The micro-reactor chip is a chip to establish reaction or biochemical analysis, such as genomic analysis, and the substrate for microanalysis is a substrate to be used for DNA analysis. Such a chip or substrate has grooves formed in microns to flow a fluid, e.g., a gas or a liquid, such as a solution, according to the mode defined in item 8). By arcuately chamfering the boundary portion of the grooved portion and the terrace-shaped flat portion formed on the chip/substrate, it is possible to prevent the grooved portion from being chipped and to prevent trouble from being caused in reaction, analysis or the like. According to the method for fabricating a glass substrate wherein the glass substrate has a grooved portion formed in a micron structure in a terrace-shaped flat portion disposed thereon, and the boundary portion between the grooved portion and the terrace-shaped flat portion disposed on the substrate is arcuately chamfered, the substrate is fabricated in a single pressing step, being subjected to heat and pressures by the mold member, which has the convex portion formed for forming the grooved portion. Accordingly, it is possible to carry out mass production since the substrate can be more easily fabricated in comparison with the method for fabricating a substrate by etching, and the method for fabricating a substrate by pressing, followed by grinding.

The mode defined in item 10) is directed to an optical fiber fixing substrate among substrates having a grooved portion. In the case of the optical fiber fixing substrate, when trouble is caused in such a way that a portion of the substrate close to the grooved portion is chipped in addition to the top of the grooved portion being chipped, there is caused a problem that the chipped portion enters the grooved portion to damage the optical fiber. From this viewpoint, in accordance with the present invention, the substrate comprises the substrate body having the grooveless flat portion, and the terrace-shaped flat portion including the grooved portion formed on the substrate and having the groove formed therein, and the bonding projections formed on both sides of the grooved portion so as to sandwich the grooved portion therebetween and to be higher than the flat portion, wherein the top of the groove, the boundary portion between the grooved portion and each of the bonding projections, and the ridge portions of the bonding projections are arcuately chamfered.

In the optical fiber fixing substrate according to item 11), each of the bonding projections has a cut-out portion formed on an outer side thereof. In other words, each of the bonding projections has the cut-out portion formed on the outer side thereof in a cross-section of the substrate, which is taken in a direction perpendicular to the forming direction of the groove (the forming direction of the top). It is possible to increase the molding precision of the groove since projections of the mold for forming the cut-out portions serve to prevent the substrate base material from laterally flowing on pressing by forming the cut-out portions as stated earlier. Accordingly, it is possible to ensure the molding precision of the groove and to establish mass production with stable quality even when fabricating plural substrates from a larger substrate. It is also possible to make the mold structure simple and to avoid an adverse effect to the quality of substrates (due to the presence of flash, positional variation or the like).

On the other hand, in the case of the optical fiber fixing substrate without cut-out portions disclosed in JP-A-11-194226, a mold is required to be configured in such a shape to confine the outer sides of flat portions on both sides of a grooved portion, that is to say, a bottom mold is required to have a barrel structure to prevent a substrate base material from laterally flowing on pressing. As a result, there is a disadvantage that the mold structure is complicated, and the mold has seams inevitably. Additionally, a top has mold no convex portion for molding the cut-out portions, that is to say, the top mold has a jointed structure formed in such a shape that both sides of each of grooves are simultaneously ground, and that the top mold is divided into base portion molding molds and a grooved portion molding mold having a different height from the base portion molding mold. Further, when plural substrates are fabricated by the mold structure disclosed in JP-A-11-194226, it is difficult to ensure required molding precision of the grooved portion since it is impossible to confine the respective outer sides of the flat portions on both sides of the grooved portion.

From the viewpoint of the mold structure stated earlier, the mode defined in item 11) is superior to the optical fiber fixing substrate disclosed in JP-A-11-194226.

In the case of the optical fiber fixing substrate according to the mode defined in item 10) or item 11) stated earlier, the bonding projections may be disposed at a higher position than the top of the groove. In such a case, the bonding projections serve as protecting members for the top of the groove to prevent the top of the groove from being inadvertently brought into contact with another member. Thus, it is possible to the top of the groove from being chipped.

According to the mode defined in item 12), the boundary portion between adjacent surfaces of each of the cut-out portions is arcuately chamfered. Accordingly, it is possible to prevent the boundary portion from being chipped and to prevent an optical fiber from being damaged by a chipped portion of the boundary portion.

In accordance with the method for fabricating an optical fiber fixing substrate according to the mode defined in item 13), the optical fiber fixing substrate is fabricated in a single pressing step, being subjected to heat and pressures by the mold member, which has the concave and convex portion for forming the grooved portion, the concave portions for forming the bonding projection, and the convex portions for forming the cut-out portions, wherein the concave and convex portion and the concave portions are formed in the indented portion surrounded by the entire periphery of the mold reference surface forming flat surfaces of the convex portions. Accordingly, it is possible to establish mass production since it is possible to fabricate the substrate more easily in comparison with the method for fabricating an optical fiber fixing substrate by etching, and the method for fabricating an optical fiber fixing substrate by pressing, followed by grinding.

EXPLANATION OF REFERENCE NUMERALS

10 . . . optical fiber fixing substrate, 12 . . . V-shaped grooved portion, 12A . . . peak, 12B . . . valley, 14 . . . substrate body, 15 . . . grooveless flat portion, 16 . . . bonding projection, 18 . . . cut-out portion, 19 . . . terrace-shaped flat portion, 20 . . . press mold, 22 and 26 . . . boundary portion, 24A and 24B . . . ridge portion, 40 . . . substrate base material, 80 . . . flat portion, 82 . . . groove, R . . . chamfer, 100 . . . press mold for fabricating a glass substrate, 101 . . . top mold, 102 . . . bottom mold, 103 . . . indented portion, 104 . . . terrace-shaped flat portion formed on a substrate, 105 . . . convex portion, 106 . . . arcuately chamfered portion formed in the boundary portion between a flat portion and a convex portion, 107 . . . mold reference surface, 110 . . . press mold for fabricating a glass substrate, 111 . . . top mold, 112 . . . bottom mold, 113 . . . indented portion, 114 . . . terrace-shaped flat portion formed on a substrate, 115 . . . convex portion, 116 . . . arcuately chamfered portion formed in the boundary between a flat portion and a convex portion, 117 . . . mold reference surface

DETAILED DESCRIPTION OF THE PREFERRED EMBODIMENTS

Preferred embodiments of the substrate with a grooved portion, the method for preparing the same and the press mold for fabricating the glass substrate, according to the present invention will be described in reference to the accompanying drawings.

Figure 1:
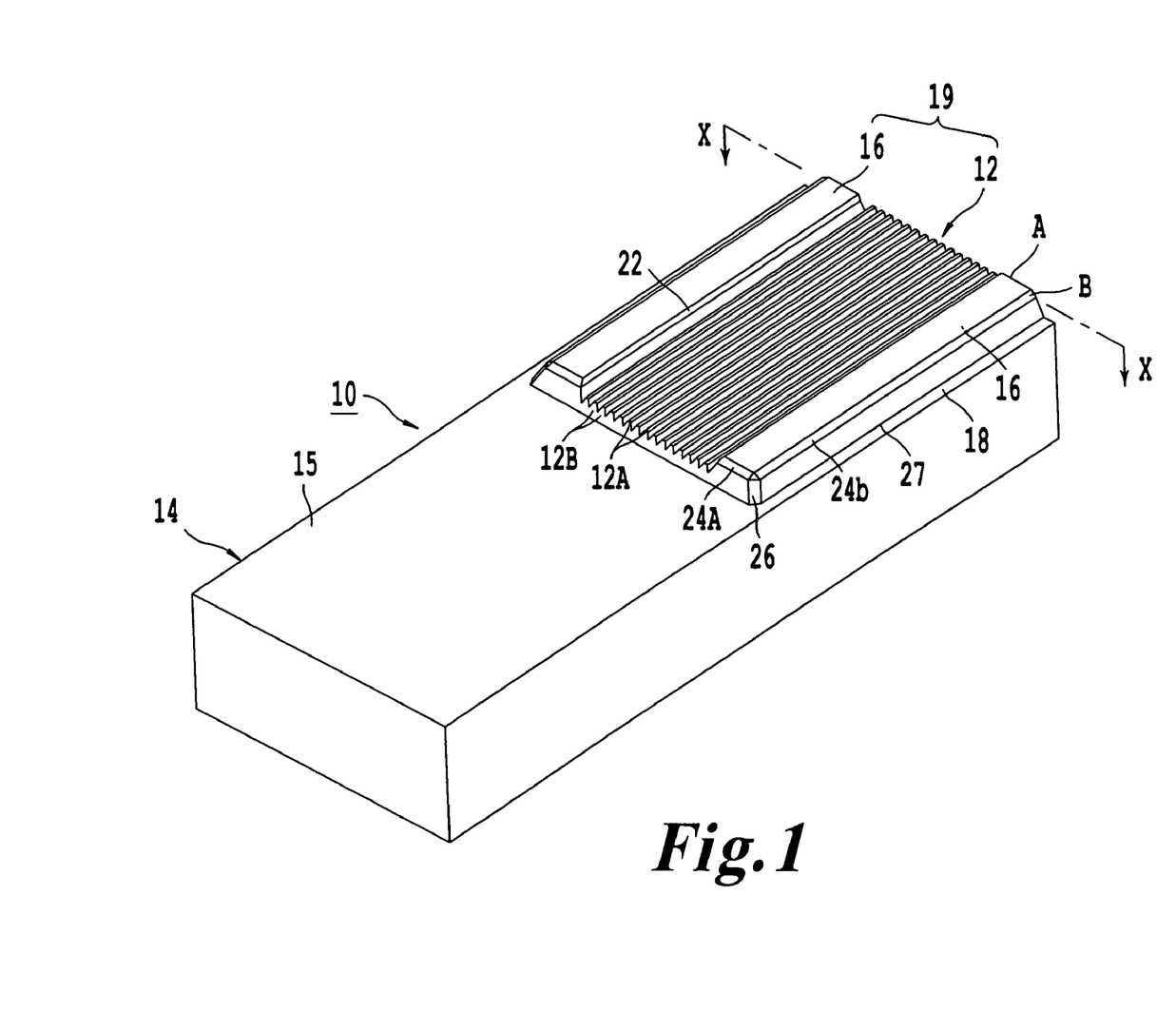
FIG. 1 is a perspective view showing the optical fiber fixing substrate according to an embodiment.

An optical fiber fixing substrate 10 as shown in FIG. 1 is configured in a substantially rectangular parallelepiped shape and has a flat portion formed with a V-shape grooved portion (grooved portion) 12 for bonding and fixing end portions of a bundle of optical fibers.

The V-shape grooved portion 12 is configured so as to have peaks 12A and valleys 12B alternatively formed therein. An example of the optical fibers bonded and fixed to valleys 12B is an optical fiber comprising a core and a clad, and having a diameter of about 130 μm. Such optical fibers are bonded and fixed to the V-shaped grooved portion 12 so as to be arrayed at equal distances on the optical fiber fixing substrate 10, V-shaped grooves being fabricated so as to have, e.g., a groove depth of 0.15 mm and a groove pitch of 0.127 mm.

Figure 2:
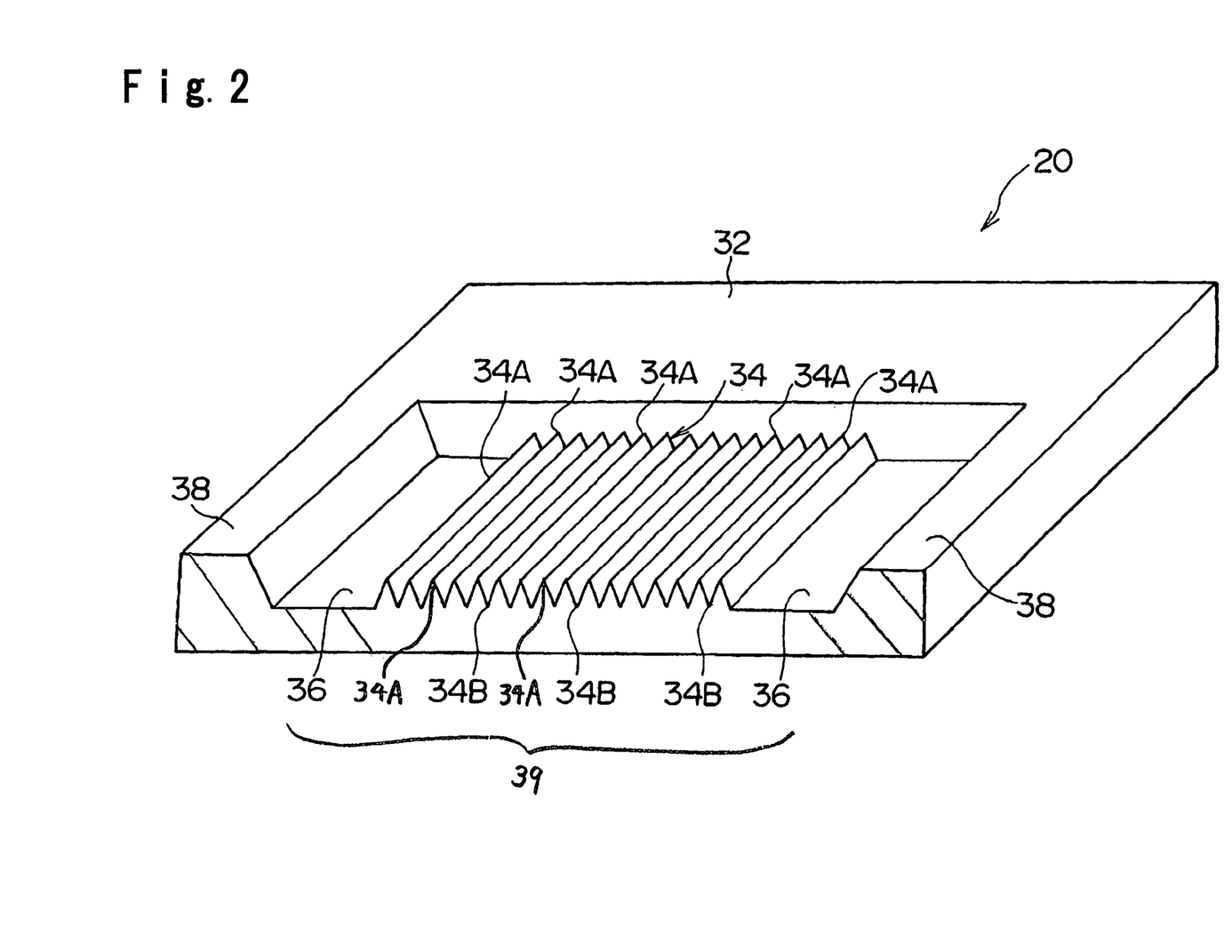
FIG. 2 is a perspective view showing a cross-section of a press mold for pressing the optical fiber fixing substrate shown in FIG. 1.

Additionally, the optical fiber fixing substrate 10 comprises a substrate body 14 having a grooveless flat portion 15 in addition to the V-shaped grooved portion 12, bonding projections 16 and 16 formed on both sides of the V-shaped grooved portion 12 so as to sandwich the V-shaped grooved portion 12 therebetween and formed to be higher than the grooveless flat portion 15, and cut-out portions 18 and 18 formed on outer sides of both bonding projections 16 and 16. The terrace-shaped flat portion 19 in this figure comprises the V-shaped grooved portion 12 and the bonding projections 16. The optical fiber fixing substrate 10 thus configured may be fabricated in a single pressing step by a press mold (mold member) 20 as shown in FIG. 2. In this figure, reference numerals 34A, 34B, 34, 36 and 38 correspond to reference numerals 12A, 12B, 12, 16 and 18 in FIG. 1. The terrace-shaped flat portion 19 corresponds to an indented portion 39, which comprises ones designated by reference numerals 34 and 36. A plane containing ones designated by reference numerals 32 and 38 forms a mold reference surface.

The optical fiber fixing substrate 10 pressed by the press mold 20 shown in FIG. 2 has respective ridge portions chamfered in an arcuate shape as shown in FIG. 1. The peaks 12A of the V-shape grooved portion 12, the boundary portion 22 between the V-shape grooved portion 12 and each of the bonding projections 16 and 16, ridge portions 24A and 24B of the bonding projections 16 and 16, and the boundary portions 26 between adjacent surfaces of cut-out portions 18 and 18. By arcuately chamfering the respective ridge portions in the vicinity of the V-shaped grooved portion 12 as stated earlier, it is possible to avoid a case wherein a ridge portion is chipped and the chipped portion enters in the V-shape grooved portion 12 to damage an optical fiber, and it is also possible to easily handle the optical fiber fixing substrate 10.

In FIG. 1, reference numeral 24A designates a ridge of a bonding projection 16 close to the grooveless flat portion 15, and reference numeral 24B designates a ridge portion of the bonding projection 16 close to the cut-out portion 18. The ridge portion A of the bonding projection 16 opposite to the ridge portion 24A and the boundary portion B opposite to the boundary portion 26 are not chamfered. This is because these portions are formed along a cutting line when the substrate 10 is cut from a substrate base material 40 stated later. Even if the ridge portion A or the boundary portion B is chipped, no significant adverse effect is caused since the cut surface of the substrate 10 with the ridge portion A and the boundary portion B not chamfered is polished after having engaged an optical fiber with the substrate 10. It should be noted that these portions may also be chamfered. By contrast, it is essential that the ridge portion 24A and the boundary portion 26 be chamfered. This is because these portions are not polished even after having engaged an optical fiber with the substrate 10. Reference numeral 27 designates the boundary portion between adjacent surfaces of a cut-out portion 18, and this boundary portion 27 may be chamfered.

The chamfered portions formed on the optical fiber fixing substrate 10 may have a radius of, e.g., 0.05 mm to 0.5 mm. The press mold 20 shown in FIG. 2 has respective corners formed in an arcuate shape in order to form the chamfered portions.

The optical fiber fixing substrate 10 may be made of a glass material, such as soda lime glass, low-alkali glass, non-alkali glass or quartz glass (synthetic quartz glass or fused quartz glass). In, e.g., the case of fixing a single optical fiber, there is a possibility that a cover to put on the optical fiber chatters. When the cover has both ends formed with legs, the cut-out portions 18 and 18 serve as receivers for the respective legs.

Figure 3:
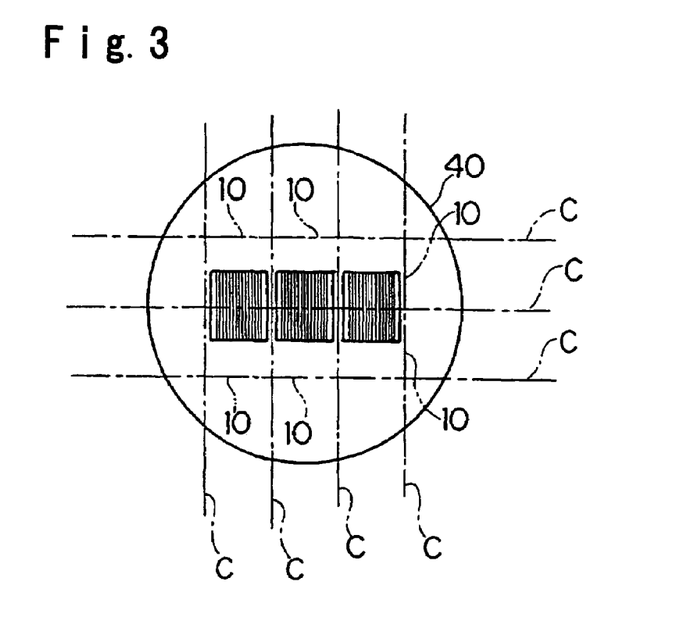
FIG. 3 is a schematic view showing that plural optical fiber fixing substrates are simultaneously pressed in a larger substrate.

In a pressing step, plural optical fiber fixing substrates (six pieces in FIG. 3) 10 may be obtained in a single pressing step by pressing the substrate base material 40, which is larger than the optical fiber fixing substrates 10 as final products as shown in FIG. 3, and followed by dicing the substrate base material 40 into small square pieces along cutting lines C indicated by dashed lines in FIG. 3.

In this case, the cutting lines C in the vertical direction in FIG. 3 extend along centerlines of convex portions forming the cut-out portions 18. For this reason, the arcuately chamfered portions of the ridge portions 24 of the bonding projections 16 have no adverse effect by dicing the substrate base material along these cutting lines C. Thus, it is possible to prevent the bonding projections 16 from being chipped. The substrate base material 40 is not limited to have the size shown in FIG. 3. For example, when a single optical fiber fixing substrate 10 is obtained by a single pressing step, the substrate base material may have a size to cope with fabrication of such a single optical fiber fixing substrate.

On the other hand, the press mold 20 shown in FIG. 2 is a seamless mold, which is formed in a plate-like shape and has a surface formed with a flat portion 32 as the mold reference surface, saw-like concave and convex portion 34 for forming the V-shaped grooved portion 12, concave portions 36 for forming the bonding projections 16, and the convex portions 38 for forming the cut-out portions 18. The flat surfaces of the convex portions 38 serve as the mold reference surface. It is preferred that each of the concave portions 36 have a bottom surface formed in a flat shape.

The press mold 20 may be made of glassy carbon or a carbon-carbon composite and be fabricated by a precision grinding machine.

Figure 4:
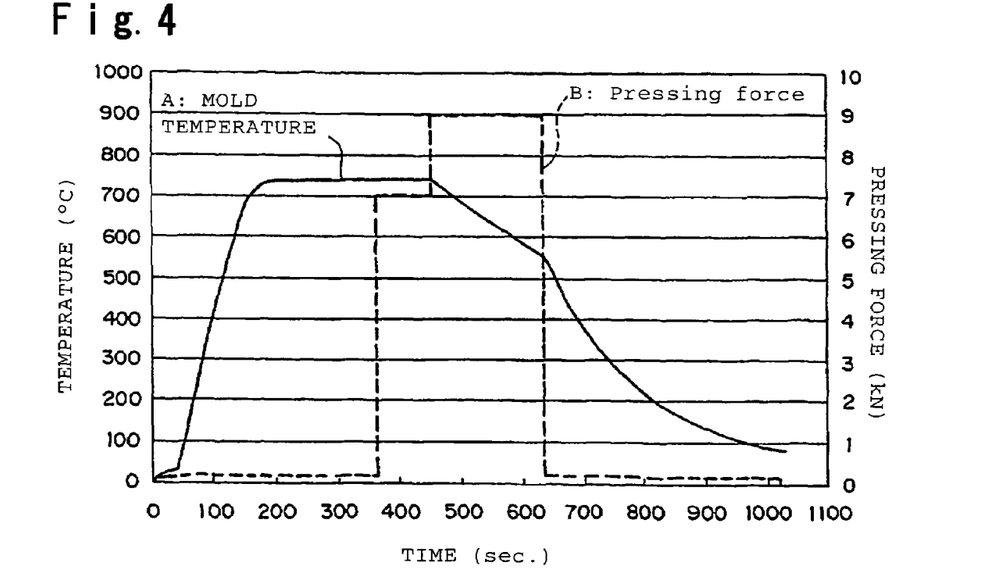
FIG. 4 is a graph showing the relationship between a pressing force and a mold temperature in a pressing step.

FIG. 4 is a graph showing changes in pressing conditions (mold temperature and pressing force) over time when pressing borosilicate glass. The vertical axes of FIG. 4 represent the mold temperature and the pressing force, and the horizontal axis represents lapsed time. Curve A is a graph showing changes in the mold temperature, and Curve B is a graph showing changes in the pressing force.

As shown in this figure, the temperature of the press mold 20 is increased to about 720° C. as the glass forming temperature until the lapse of about 150 sec after the commencement of the pressing step. After that, the temperature of about 720° C. is maintained until the lapse of about 450 sec, the temperature is gradually decreased after the lapse of about 450 sec, and the temperature is more steeply decreased so as to depict a parabolic curve after the lapse of about 630 sec. Then, the pressed glass and the press mold are separated from each other to take out the pressed substrate base material 40.

On the other hand, with respect to the pressing force, the pressing force is maintained at 0.2 kN until the lapse of about 360 sec after the commencement of the pressing step, and the pressing force is suddenly increased to 7 kN after the lapse of about 360 sec. Then, the pressing force is maintained at 7 kN until the lapse of about 450 sec, and the pressing force is suddenly increased to 9 kN after the lapse of about 450 sec. Then, the pressing force is maintained at 9 kN until the lapse of about 630 sec, and the pressing force is suddenly decreased to 0.2 kN after the lapse of about 630 sec. The pressing force is maintained at 0.2 kN until completion of the pressing step. By controlling the mold temperature and the pressing force as shown in FIG. 4, it is possible to obtain an undistorted optical fiber fixing substrate 10 from the substrate base material 40 made of glass.

As stated earlier, in accordance with the optical fiber fixing substrate 10 in this embodiment, the tops 12A of the V-shape grooved portion 12, the boundary portion 22 between the V-shaped grooved portion 12 and each of the bonding projections 16 and 16, the ridge portions 24A and 24B of the bonding projections 16 and 16, and the boundary portion 26 between adjacent surfaces of the cut-out portions 18 and 18 are arcuately chamfered as shown in FIG. 1. Accordingly, it is possible to avoid a case wherein a ridge portion is chipped, and the chipped part enters the V-shaped grooved portion 12 to damage an optical fiber. Additionally, it is possible to easily handle the optical fiber fixing substrate 10.

The optical fiber fixing substrate 10 may be configured so that the bonding projections 16 and 16 are set so as to be higher than the tops 12A of the V-shaped grooved portion 12. In this case, the bonding projections 16 and 16 can serve as protection members for the tops 12A of the V-shaped grooved portion 12, avoiding a case wherein a top 12A of the V-shaped grooved portion 12 is chipped by inadvertent contact of the top 12A of the V-shaped grooved portion 12 with another member. The optical fiber fixing substrate 10 shown in FIG. 1 is configured so that the bonding projections 16 and 16 are set so as to be higher than the tops 12A of the V-shaped grooved portion 12.

Additionally, the optical fiber fixing substrate 10 has the cut-out portions 18 and 18 formed so as to extend along the longitudinal direction of the bonded projections 16 and 16 on the outer sides of both bonding projections 16 and 16. In other words, the cut-out portions 18 as stepped portions are formed on the outer sides of both bonding projections 16 in a cross-section of the optical fiber fixing substrate 10 taken in a direction perpendicular to the forming direction of the tops 12A (the cross-section taken along line X-X in FIG. 1).

Since the cut-out portions 18 are formed as stated earlier, the convex portions 38 of the press mold 20 for forming the cut-out portions 18 serve to prevent the substrate base material from laterally flowing on pressing, increasing the molding precision of the V-shaped grooved portion 12. Accordingly, it is possible to ensure the required molding precision of the V-shaped grooved portion 12 and to do mass production with stable quality even when plural optical fiber fixing substrates 10 are fabricated from the substrate base material 40 having a greater size as shown in FIG. 3. Since the pressing step can be performed by the seamless mold, it is possible to simplify the mold structure and to avoid an adverse effect to the quality of an optical fiber fixing substrate by the presence of a seam in the mold (such as the occurrence of a flash or a positional variation).

In accordance with the method for fabricating the optical fiber fixing substrate 10, the seamless press mold 20, which includes the saw-like concave and convex portion 34 for forming the V-shaped grooved portion 12, the concave portions 36 for forming the bonding projections 16, and the convex portions 38 for forming the cut-out portions 18, is used to the optical fiber fixing substrate 10 in a single pressing step while applying heat and pressures to the substrate.

Thus, it is possible to do mass production since it is possible to more simply fabricate the optical fiber fixing substrate 10 in comparison with the method for fabricating an optical fiber fixing substrate by etching, and the method for fabricating an optical fiber fixing substrate by pressing, followed by grinding.

By the way, a micro-reactor chip or a substrate for microanalysis has been known as a substrate made of a glass material having grooves formed in a micron structure (in microns) as in the optical fiber fixing substrate 10.

Figure 5:
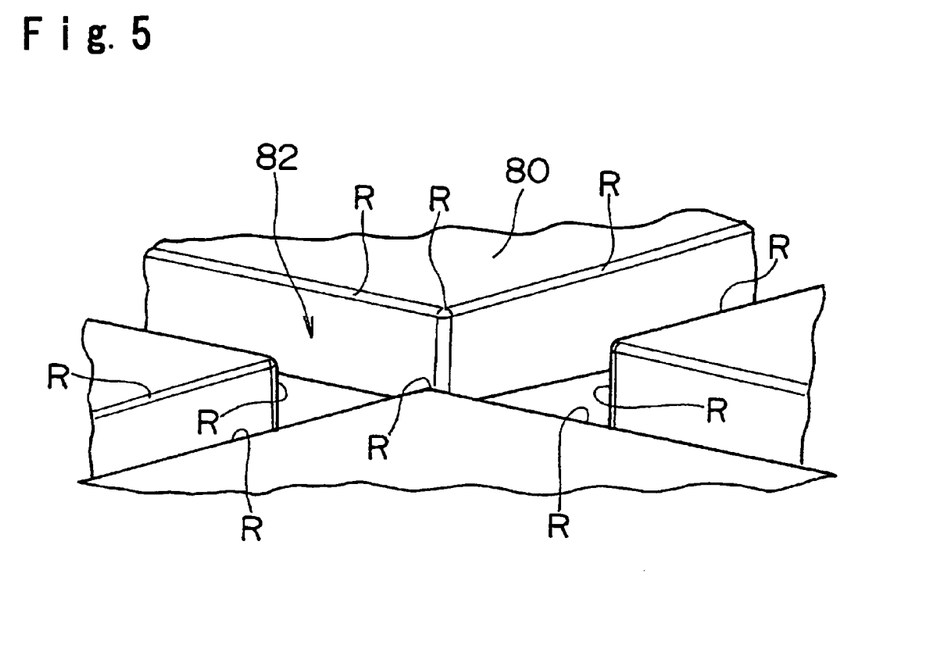
FIG. 5 is an enlarged view of flow passages formed in a micro-reactor chip or a substrate for microanalysis.

In such a micro-reactor or a substrate for microanalysis, the substrate has a terrace-shaped flat portion 80 formed with grooves 82 in microns to flow, e.g., a gas or a liquid, such as a solution, as shown in FIG. 5. When a groove 82 is chipped, trouble is caused in reaction or analysis.

Since the boundary portion between each of the grooves 82 and the terrace-shaped flat portion 80 formed on the substrate as shown in FIG. 5 is arcuately chamfered as indicated by R, it is possible to restrain the grooves 82 from being chipped.

It is possible to fabricate even a micro-reactor chip or a substrate for microanalysis in mass production since it is possible to fabricate such a chip or substrate in a single pressing step while applying heat and pressures by a mold member having convex portions formed thereon for forming the grooves 82.

Figure 6:
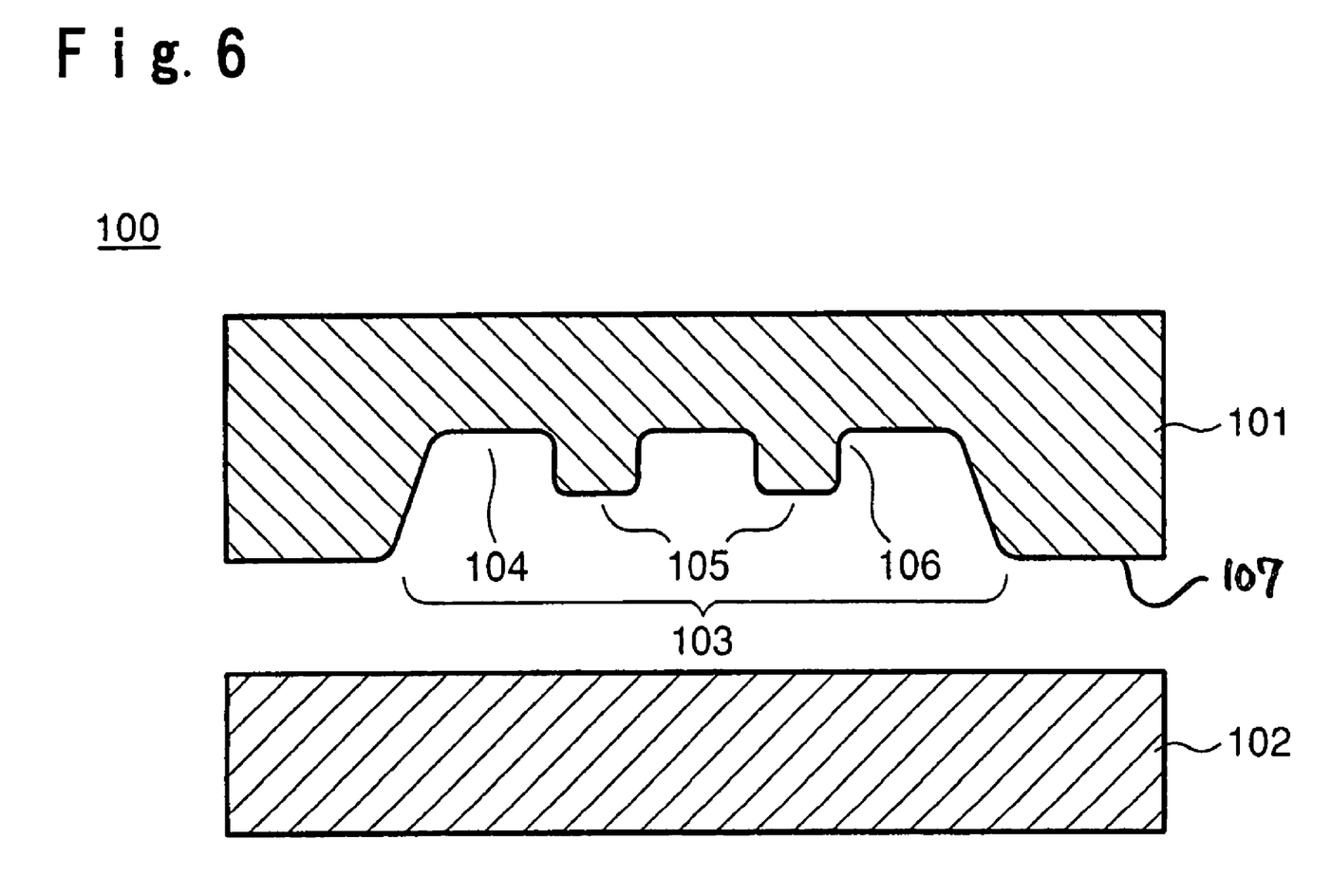
FIG. 6 is a cross-sectional view of a press mold for fabricating a glass substrate having a bathtub structure.
Figure 7:
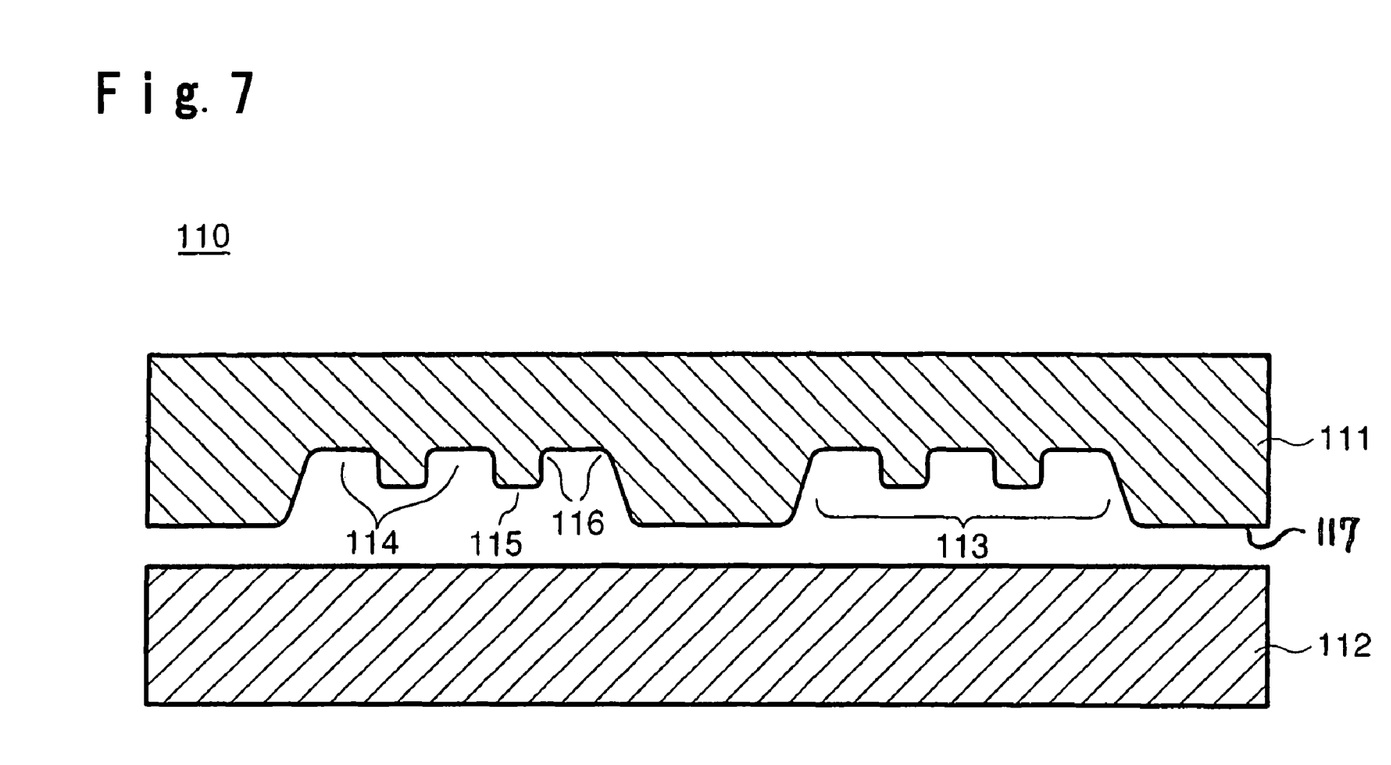
FIG. 7 is a cross-sectional view of a press mold for fabricating a glass substrate having plural bathtub structures.

The press mold 100 for glass shown in FIG. 6 includes a top mold 101 and a bottom mold 102. The top mold 101 has an indented portion 103 formed thereon, and the indented portion 103 has convex portions 105 formed so as to a grooved portion (hereinbelow, referred to as the bathtub structure in some cases). A mold reference surface 107 is provided so as to surround the entire periphery of the indented portion 103. It is preferred that the indented portion 103 have flat surfaces 104 formed therein. The boundary portion between the indented portion 103 (a flat surface 104 in this figure) and the convex portion 105 adjacent the flat surface has an arcuately chamfered portion 106 formed thereon. The press mold 110 for glass shown in FIG. 7 is related to a case wherein a bathtub structure is formed at plural locations. In the case of FIG. 7 as well, indented portions 113 have flat surfaces 114 formed therein, and convex portions 115 are formed on each of the flat surfaces 114 so as to correspond to grooved portions. The boundary portion between a flat surface 114 and its adjacent convex portion 115 has an arcuately chamfered portion 116 formed thereon. A mold reference surface 117 is provided so as to surround the entire periphery of the indented porticos 113. The mold reference surface is normally a mating surface, on which the molding surfaces of the top mold and the bottom mold are mated together.

INDUSTRIAL APPLICABILITY

As explained, in accordance with the glass substrate with the grooved portion according to the present invention, it is possible to prevent the grooved portion from being chipped since the boundary portion between the grooved portion in a micron structure and the terrace-shaped flat portion formed on the glass substrate, such as a micro-reactor chip or a substrate for microanalysis, is arcuately chamfered.

In accordance with the method for fabricating the glass substrate with the grooved portion according to the present invention, the glass substrate is fabricated in a single pressing step, being subjected to heat and pressures by the mold member having a convex portion formed thereon for forming the grooved portion. Accordingly, it is possible to fabricate the substrate more easily and in mass production in comparison with the method for fabricating a substrate by etching, and the method for fabricating a substrate by pressing, followed by grinding.

By using the press mold for fabricating the glass substrate, according to the present invention, it is possible to fabricate easily and in mass production the substrate, which has molding precision required for, e.g., a micro-reactor chip.

In accordance with the optical fiber fixing substrate according to the present invention, the glass substrate comprises the substrate body having the grooveless flat portion, the grooved portion having grooves formed thereon, the bonding projections formed on both sides of the grooved portion so as to sandwich the grooved portion therebetween and to be higher than the tops of the grooves, and the cut-out portions formed on the outer sides of the bonding projections, wherein the tops of the grooves, the boundary portion between the grooved portion and each of the bonding projections, the ridge portions of the bonding projections, and the boundary portion between adjacent surfaces of the cut-out portions are arcuately chamfered. Accordingly, it is possible to prevent the optical fiber fixing substrate from being chipped to damage an optical fiber.

In accordance with the method for fabricating the optical fiber fixing substrate, according to the present invention, the optical fiber fixing substrate is fabricated in a single pressing step, being subjected to heat and pressures by the mold member, which has the concave and convex portion for forming the grooved portion, the concave portions for forming the bonding projections, and the convex portions for forming the cut-out portions. Accordingly, it is possible to fabricate the optical fiber fixing substrate easily and in mass production.

The press mold for fabricating the glass substrate, according to the present invention has the bathtub structure formed therein. Accordingly, glass as an object to be molded is molded in the indented portion, being confined in the indented portion. Thus, it is possible to fabricate the glass substrate with excellent molding precision since the terrace-shaped flat portion, the convex portions and others are accurately transferred onto the glass substrate. In particular, when the bathtub structure is disposed at plural locations in a single press mold, the effect offered by the press mold is significant.

This application is based upon and claims the benefit of priority under 35 U.S.C. § 120 from Application Ser. No. PCT/JP2004/004200, filed Mar. 25, 2004, and under 35 U.S.C. § 119 from Japanese Patent Application No. 2003-082634 filed on Mar. 25, 2003, the entire contents of each of which including specification, claims, drawings and summary is incorporated herein by references in its entirety.

What is claimed is:

1. A glass substrate comprising:
    a substrate;
    a terrace-shaped flat portion formed on the substrate and having at least one bonding projection and a grooved portion formed in a micron structure therein; and
    a boundary portion adjacent to the terrace-shaped flat portion formed on the substrate, the boundary portion being arcuately chamfered,
    wherein the bonding projection is higher in a vertical direction than a top of the grooved portion.

2. The glass substrate according to claim 1, wherein the grooved portion is configured to allow fluid to flow therebetween.

3. The glass substrate according to claim 2, configured as a micro-reactor chip or a substrate for microanalysis.

4. An optical fiber fixing substrate comprising:
    a substrate body having a flat portion; and
    a terrace-shaped flat portion including
        a grooved portion formed on the substrate having at least one groove formed in the grooved portion, the grooved portion configured to fix an end portion of an optical fiber, and
    bonding projections formed on both sides of the grooved portion and adjacent to the grooved portion so as to sandwich the grooved portion therebetween and to be higher than the flat portion and a top of the at least one groove,
    wherein the top of the at least one groove, a boundary portion between adjacent to the grooved portion and each of the bonding projections, and ridge portions of the bonding projections are arcuately chamfered.

5. The optical fiber fixing substrate according to claim 4, wherein each of the bonding projections has a cut-out portion formed on an outer side thereof.

6. The optical fiber fixing substrate according to claim 5, wherein a boundary portion between adjacent surfaces of the cut-out portion is arcuately chamfered.

7. A method for fabricating an optical fiber fixing substrate, comprising:
    applying heat and pressures to the substrate in a single pressing step by a mold member, the optical fiber fixing substrate defined in claim 4, and the mold member having a concave and convex portion for forming the grooved portion, concave portions for forming the bonding projections, and convex portions for forming cut-out portions,
    wherein the concave and convex portion and the concave portions are formed in an indented portion surrounded by an entire periphery of a mold reference surface forming flat surfaces of the convex portions.

* * * * *